United States Patent [19]

Sakamoto

[11] Patent Number: 4,988,592
[45] Date of Patent: Jan. 29, 1991

[54] PHOTOSENSITIVE MEMBER CONTAINING PHTHALOPERINONE OR NAPHTHALIMIDE

[75] Inventor: Mitsutoshi Sakamoto, Osaka, Japan

[73] Assignee: Minolta Camera Kabushiki Kaisha, Osaka, Japan

[21] Appl. No.: 417,186

[22] Filed: Oct. 4, 1989

[30] Foreign Application Priority Data

Oct. 5, 1988 [JP] Japan .................. 63-252624

[51] Int. Cl.$^5$ ............................. G03G 5/14
[52] U.S. Cl. ......................... 430/58; 430/78; 430/83
[58] Field of Search ............ 430/76, 78, 83, 58, 430/59

[56] References Cited

U.S. PATENT DOCUMENTS 4,450,218  5/1984  Takei et al. .................. 430/59

FOREIGN PATENT DOCUMENTS 56-95241  8/1981  Japan .
61-35452  2/1986  Japan .
61-77054  4/1986  Japan .

Primary Examiner—David Welsh
Attorney, Agent, or Firm—Burns, Doane, Swecker & Mathis

[57] ABSTRACT

This invention relates to a photosensitive member having a photosensitive layer wherein the photosensitive layer comprises a charge generating material, a phthaloperinone compound represented by the general formula [I] or [I'] below, and/or naphthalimide represented by the general formula [II] or ]II'] below;

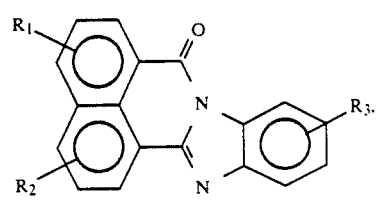

[I]

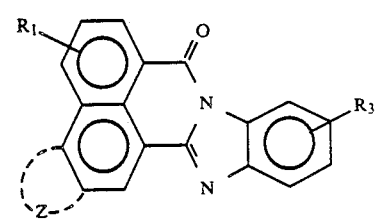

[I']

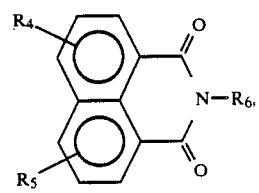

[II]

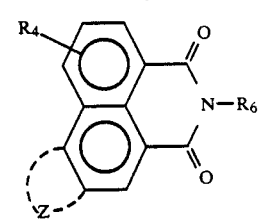

[II']

wherein $R_1$, $R_2$, $R_3$, $R_4$ and $R_5$ are respectively a hydrogen atom, an alkyl group, an amino group, a hydroxy group, a halogen atom, a nitro group, or a cyano group; $R_6$ is a hydrogen atom, an alkyl group or an aryl group; Z is a residual group forming a condensed aromatic cyclic ring with a benzene ring and Z may have a substitutent.

13 Claims, No Drawings

PHOTOSENSITIVE MEMBER CONTAINING PHTHALOPERINONE OR NAPHTHALIMIDE

BACKGROUND OF THE INVENTION

This invention relates to a photosensitive member containing a phthaloperinone compound or a naphthalimide compound.

Known photosensitive materials for forming a photosensitive member include inorganic photoconductive materials such as selenium, cadmium sulfide or zinc oxide.

These photosensitive materials have many advantages such as low loss of charges in the dark, an electrical charge which can be rapidly dissipated with irradiation of light and the like. However, they have disadvantages. For example, a photosensitive member based on selenium is difficult to produce, has high production costs and is difficult to handle due to inadequate resistivity to heat or mechanical impact. A photosensitive member based on cadmium sulfide or zinc oxide has defects such as its unstable sensitivity in a highly humid environment and loss of stability with time because of the deterioration of dyestuffs, added as a sensitizer, by corona charge and fading with exposure.

Many kinds of organic photoconductive materials such as polyvinylcarbazole and so on have been proposed. These organic photoconductive materials have superior film forming properties, are light in weight, etc., but inferior in sensitivity, durability and environmental stability compared to the aforementioned inorganic photoconductive materials.

Various studies and developments have been in progress to overcome the above noted defects and problems. A function-divided photosensitive member of a laminated or a dispersed type has been proposed, in which charge generating function and charge transporting function are divided by different layers of different dispersed materials. The function-divided photosensitive member can be a highly efficient photosensitive member in electrophotographic properties such as chargeability, sensitivity, residual potential, durability with respect to copy and repetition, because most adequate materials cab be selected from various materials. Further, function-divided photosensitive members have high productivity and low costs, since they can be prepared by coating, and suitably selected charge generating materials can freely control a region of photosensitive wavelength. Illustrative examples of such charge generating materials are organic pigments or dyes such as phthalocyanine pigment, azo pigment, polycyclic quinone pigment, perylene pigments and the like.

However, such photosensitive members, which satisfy general static property requirements are not produced easily, and more improved sensitivity is desired.

SUMMARY OF THE INVENTION

The object of the invention is to provide a photosensitive member containing a charge generating material excellent in stability of charging potential and repetition properties.

This invention relates to a photosensitive member having a laminated photosensitive layer constituted of a charge generating layer and a charge transporting layer on an electrically conductive substrate, wherein the charge generating layer comprises a charge generating material, wherein a phthaloperinone compound represented by the general formula [I] or [I'] below, and/or a naphthalimide represented by the general formula [II] or [II'] below;

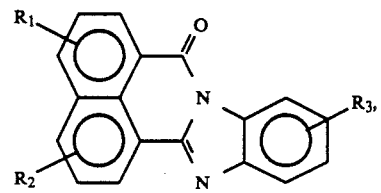

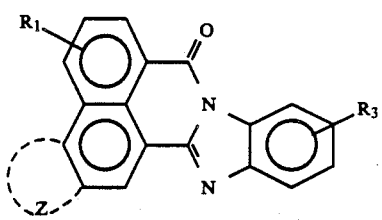

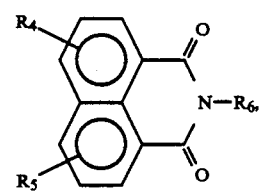

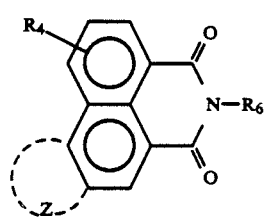

wherein $R_1$, $R_2$, $R_3$, $R_4$ and $R_5$ are respectively a hydrogen atom, an alkyl group, an amino group, a hydroxy group, a halogen atom, a nitro group, or a cyano group; $R_6$ is a hydrogen atom, an alkyl group or an aryl group; Z is a residual group forming a condensed aromatic cyclic ring with a benzene ring and Z may have a substituent.

DETAILED DESCRIPTION OF THE INVENTION

This invention provides a photosensitive member with a photosensitive layer containing a charge generating layer, wherein the photosensitive member further comprises a phthaloperinone compound represented by the general formula [I] or [I'] below, and/or a naphthalimide represented by the general formula [II] or [II'] below;

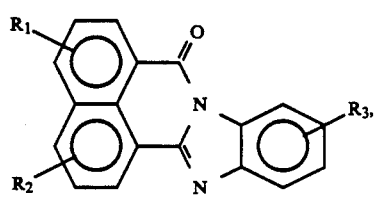

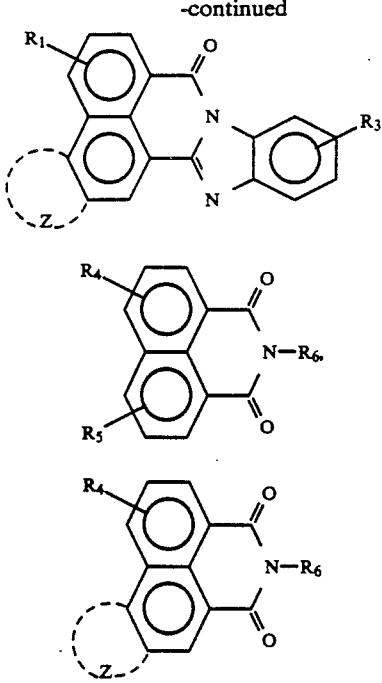

wherein $R_1$, $R_2$, $R_3$, $R_4$ and $R_5$ are respectively a hydrogen atom, an alkyl group, an amino group, a hydroxy group, a halogen atom, a nitro group, or a cyano group; $R_6$ is a hydrogen atom, an alkyl group or an aryl group; Z is a residual group forming a condensed aromatic cyclic ring with a benzene ring and Z may have a substituent.

Such a phthaloperinone compound and/or a naphthalimide compound works to aid the migration of charges generated by a charge generating material and restrain the accumulation of charges in a photosensitive member, resulting in the prevention of the decrease of the charging potential even after repeatedly used.

With respect to a charge generating, anyone known may be used, and particularly exemplified in no way restrictive by azo compounds such as monoazo compounds, bisazo compound, trisazo compound and the like, metal phthalocyanine, metal-free phthalocyanine, polycyclic quinones, perylene and the like.

With respect to an amount of a phthaloperinone compound and/or a naphthalimide compound contained in a photosensitive layer, those compounds are added at the content of 0.01-10 parts by weight, preferably 0.1-1 part by weight on the basis of 1 part by weight of a charge generating compound. If the amount is low so much, the effects of the invention can not be appreciated. If the content in high so much, a dispersion stability of an application solution for the formation of a photosensitive layer on an electrically conductive substrate becomes poor and the adhesive properties becomes also poor, and that even if a photosensitive layer is formed at such high content, the obtained photosensitive member has such a problem as the increase of residual potential.

With respect to the structure of a photosensitive member, it may be a monolayer type in which a photosensitive layer is formed on an electrically conductive substrate by dispersing a charge generating compound, a phthaloperinone compound and/or naphthalimide compound and if necessary, a charge transporting material, or preferably a laminated type in which a photosensitive layer is a function divided type and formed by laminating a charge generating layer on an electrically conductive substrate and then laminating a charge transporting layer on the charge generating layers, or in reverse by laminating a charge generating layer on a charge transporting layer on an electrically conductive substrate a laminated type effects the improvement of sensitivity, charging properties surface strength and the like required for a photosensitive member.

Further an undercoat layer and/or a surface protective layer may be included in a photosensitive member, if desired.

An electrically conductive substrate is exemplified by a sheet or a drum made of metal or alloy such as copper, aluminium, silver, iron, and nickel; a substrate such as plastic film on which the foregoing metal or alloy is adhered by a vacuum-deposition method or an electroless plating method and the like; a substrate such as a plastic film and paper on which and electroconductive layer is formed by applying or depositing electroconductive polymer, indium oxide, tin oxide etc..

In general, when a charge generating layer is formed on an electrically conductive substrate, a charge generating compound as above mentioned is dispersed in a solution containing a binder resin in an appropriate solvent and the dispersion is applied on an electrically conductive substrate followed by drying.

In order to incorporate a phthaloperinone compound and/or a naphthalimide compound into a charge generating layer, phthaloperinone compound and/or the naphthalimide compound may be added into a dispersed solution above mentioned, adsorbed into charge generating-material particles prior to dispersion, added at the same time of application of a dispersed solution, or adsorbed into a charge generating layer after a dispersed solution was applied on an electrically conductive substrate.

Applicable as a binder resin for the production of a photosensitive layer are any of thermoplastic resins, thermosetting resins, photo curing resins and photoconductive resins, which are publicly known to be electrically insulative.

Some examples of binders are shown by with no significance in restricting the embodiment of the invention, by polyester, polyvinylbutyral, polyvinylacetal, (metha)acrylic resin, polyvinyl chloride, copolymer of vinyl chloride-vinylacetal, polyvinylidene chloride, alkyd resin, urethane resin, phenol resin, phenoxy resin, a mixture thereof.

Applicable as a charge transporting material for the production of a charge transporting layer are positive-hole-transporting compounds such as anthracene, pyrene, a carbazole derivative, a tetrazole derivative metallocene, a phenothiazine derivative, pyrazoline, a hydrazone compound, a styryl compound, a styrylhydrazone compound, a thiazole compound, an oxazole compound, an oxadiazole compound, a imidazole compound, a phenylenediamime derivative, a stilbene derivative and a polymer thereof.

Applicable as a binder resin for the production of a charge transporting layer are any of thermoaplastic resins, thermosetting resins, photocuring resins and photoconductive resin, which are publicly known to be electrically insulative, being the same as those described on the resins for the formation of a charge generating layer. Some examples are shown with no significance in restricting the embodiment of the invention by polymer or copolymer of (metha)acrylic monomer, acrylonitrile, styrene, butadiene, vinyl acetate, vinyl chloride and the like, polycarbonates, polyarylates, polyesters, polysulfones, polyethersulfones, polyamides, epoxy resins, urethane reisns, alkyd resins, silicone resins or a mixture thereof.

EXAMPLE 1

One part by weight of α-type titanyl phthalocyanine as a charge generating material, one part by weight of polyvinylbutyral (S-Lec BL-S) and 98 parts by weight of cyclohexanone were mixed for dispersion in a paint conditioner for 3 hours. Then 0.3 parts by weight of 12H-phthaloperinone represented by the formula (1) below was added to the above obtained dispersed solution to prepare an application solution for a charge generating layer.

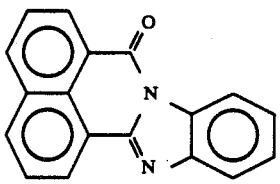

(1)

A cylindrical aluminium drum was dipped in the application solution so that a charge generating layer of 0.2 μm in thickness might be formed thereon after dried.

Then 10 parts by weight of the butadiene compound as a charge transporting material represented by the formula (2) below;

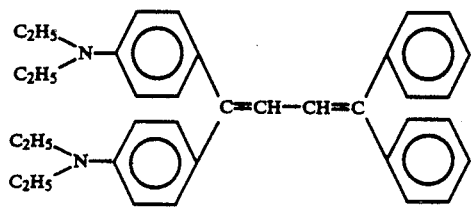

(2)

were dissolved in a solution of polycarbonate (10 parts by weight) (K-1300; made by Teijin Kase K. K.) in dichloromethane of 90 parts by weight to prepare an application solution for a charge transporting layer.

A charge generating layer formed on the cylindrical aluminium drum was dipped in the application solution above obtained so that a charge transporting layer of 20μm in thickness might be formed on the charge generating layer after dried. Thus, a photosensitive member with two layers as a photosensitive layer was prepared.

EXAMPLE 2

A photosensitive member of function-divided type with a charge generating layer and a charge transporting layer was prepared in a manner similar to Example 1 except that 1 part by weight of 12H-phthaloperinone of the formula (1) was used.

EXAMPLE 3

A photosensitive member of function-divided type with a charge generating layer and a charge transporting layer was prepared in a manner similar to Example 1 except that N-methyl-1,8-naphthalimide represented by the formula (3);

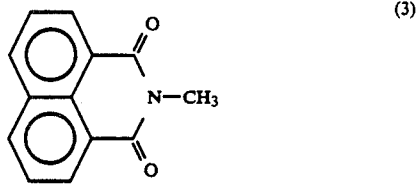

(3)

was added to the dispersed solution for the preparation for a charge generating layer instead of 12H-phthaloperinone of the formula (1).

EXAMPLE 4

A photosensitive member of function-divided type with a charge generating layer and a charge transporting layer was prepared in a manner similar to Example 1 except that ε-type copper phthalocyanine was used as a charge generating material instead of α-type titanyl phthalocyanine.

EXAMPLE 5

A photosensitive member of function-divided type with a charge generating layer and a charge transporting layer was prepared in a manner similar to Example 1 except that the bisazo compound represented by the formula (4) below;

was used as a charge generating material instead of α-tytanyl phthalocyanine.

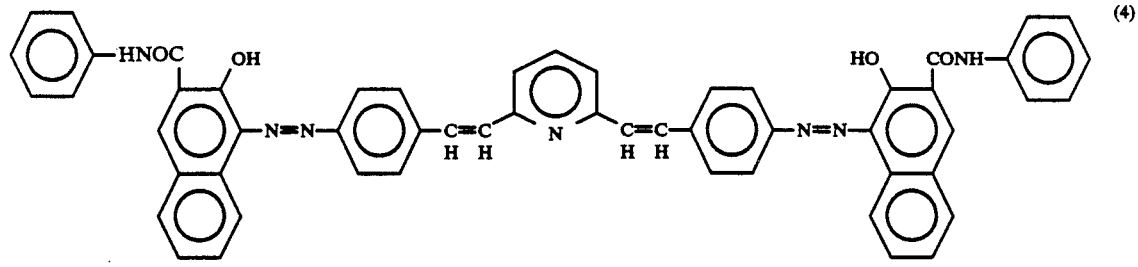

(4)

COMPARATIVE EXAMPLE 1

A photosensitive member of function-divided type with a charge generating layer and a charge transporting layer was prepared in a manner similar to Example 1 except that 12H-phthaloperinone of the formula (1) was not added to the dispersed solution for the preparation for a charge generating layer.

COMPARATIVE EXAMPLE 2

A photosensitive member of function-divided type with a charge generating layer and a charge transporting layer was prepared in a manner similar to Example 1 except that ε-type phthalocyanine was used as a charge generating material and that 12H-phthaloperinone of the formula (1) was not added to the dispersed solution for the preparation for a charge generating layer.

COMPARATIVE EXAMPLE 3

A photosensitive member of function-divided type with a charge generating layer and a charge transporting layer was prepared in a manner similar to Example 1 except that the bisazo compound of the formula (4) above described was used as a charge generating material and that 12H-phthaloperinone of the formula (1) was not added to the dispersed solution for the preparation for a charge generating layer.

Evolution

Initial surface potential Vo[V] and exposure amount for half-reduction E1/2 (which is the exposure amount required for the surface potential to be half the value of the initial surface potential) were measured on the above obtained photosensitive members.

After 3000 times repetitions of charging and charge-removing process, Vo and E1/2 were also measured to evaluate repetition stability.

By the way, the evolutions on the photosensitive members obtained in Examples 1-4 and Comparative Examples 1-2 were made with a converted laser beam printer (SP-348; made by Nissho Electronics K. K.) available in the market.

A photosensitive member was installed in the converted laser printer to measure Vo and E1/2 (Erg/cm$^2$), in which grid potential of scorotoron charger was adjusted so that a photosensitive member might be charged at about −700 V.

The evoluations in the photosensitive members obtained in Example 5 and Comparative Example 3 were make with a converted copier (EP-470Z; made by Minolta Camera K. K.) available in the market to measure Vo[V]and E1/2 (lux sec) similarly as above.

As understood from the results shown in Table 1 and Table 2, photosensitive members of the present invention excellent in repetition stability because Vo and E1/2 varied little even after 3000 times repetions.

The results were shown in Table 1 and Table 2.

TABLE 1

|  | initial properties | | after 3000 times | |
| --- | --- | --- | --- | --- |
|  | Vo (V) | E½ erg/cm$^2$ | Vo (V) | E½ erg/cm$^2$ |
| Example 1 | −700 | 3.3 | −670 | 3.0 |
| Example 2 | −710 | 3.0 | −690 | 2.9 |
| Example 3 | −710 | 3.5 | −690 | 3.4 |
| Example 4 | −700 | 17.0 | −680 | 16.0 |
| Comparative example 1 | −700 | 3.3 | −500 | 2.6 |
| Comparative example 2 | −705 | 16.5 | −480 | 11.0 |

TABLE 2

|  | initial properties | | after 3000 times | |
| --- | --- | --- | --- | --- |
|  | Vo (V) | E½ lux · sec | Vo (V) | E½ lux · sec |
| Example 5 | −610 | 4.2 | −590 | 4.0 |
| Comparative example 3 | −600 | 4.1 | −420 | 2.8 |

What is claimed is:

1. A photosensitive member having a laminated photosensitive layer constituted of a charge generating layer and a charge transporting layer on an electrically conductive substrate, wherein the charge generating layer comprises a charge generating material and an additive selected from the group consisting of a phthaloperinone compound represented by the general formula [I] below, a phthaloperinone compound represented by the general formula [I'] below, a naphthaline compound represented by the general formula [II] and a naphthalimide compound represented by the general formula [II'] below:

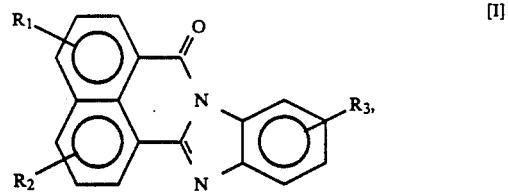

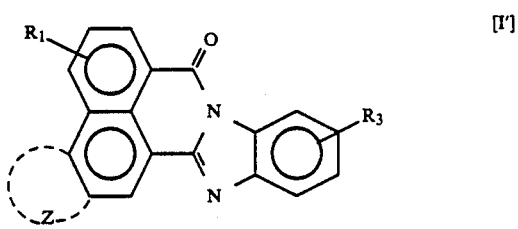

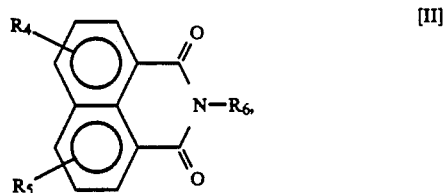

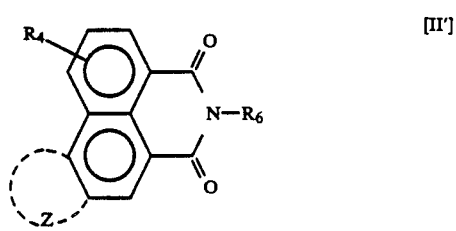

wherein $R_1$, $R_2$, $R_3$, $R_4$ and $R_5$ are respectively a hydrogen atom, an alkyl group, an amino group, a hydroxy group, a halogen atom, a nitro group, or a cyano group; $R_6$ is a hydrogen atom, an alkyl group or an aryl group; Z is a residual group forming a condensed aromatic cyclic ring with a benzene ring and Z may have a substituent.

2. A photosensitive member of claim 1 wherein the phthaloperinone compound and/or a naphthalimide compound is contained at the content of 0.01-10 parts by weight on the basis of one part by weight of the charge generaing material.

3. A photosensitive member of claim 1, wherein the charge generating material is α-type titanyl phthalocyanine.

4. A photosensitive member of claim 1, wherein, the charge generating material is ε-type copper phthalocyanine.

5. A photosensitive member of claim 1, wherein the charge generating material is a bisazo pigment.

6. A photosensitive member of claim 1, wherein the phthaloperinone compound is 12H-phthaloperinone represented by the formula below;

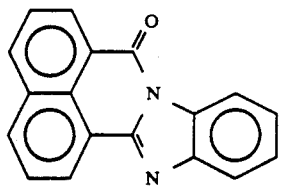

7. A photosensitive member of claim 1, wherein the naphtalimide compound is 1-methyl-1,8-naphthalimide represented by the formula below;

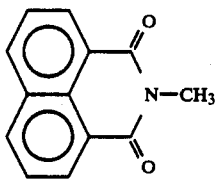

8. A photosensitive member of claim 1, wherein the charge generating layer is formed on the charge transporting layer which is formed on the substrate.

9. A photosensitive member of claim 1, wherein the charge transporting layer is formed on the charge generating layer which is formed on the substrate.

10. A photosensitive member having a photosensitive layer with at least a charge generating material and an additive dispersed in a resin on an electrically conductive substrate, said additive selected from the group consisting of a phthaloperinone compound represented by the general formula [I] below, a phthaloperinone compound represented by the general formula [I'] below, a naphthalimide compound represented by the general formula [II] and a naphthalimide compound represented by the general formula [II'] below:

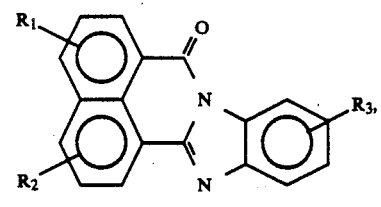

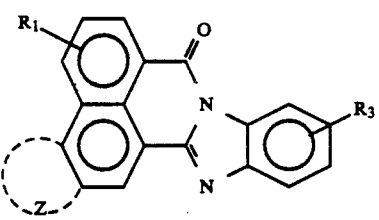

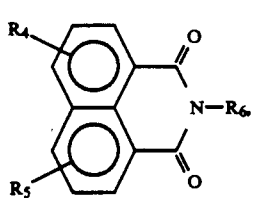

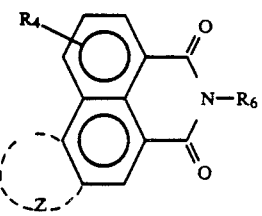

wherein $R_1$, $R_2$, $R_3$, $R_4$ and $R_5$ are respectively a hydrogen atom, an alkyl group, an amino group, a hydroxy group, a halogen atom, a nitro group, or a cyano group; $R_6$ is a hydrogen atom, an alkyl group or an aryl group; Z is a residual group forming a condensed aromatic cyclic ring with a benzene ring and Z may have a substituent.

11. A photosensitive member of claim 1, wherein the photosensitive layer further comprises a charge transporting material.

12. A photosensitive member of claim 1, wherein the phthaloperinone compound and/or the naphthalimide compound is added at the content of 0.01–10 parts by weight on the basis of one part of the charge generating material.

13. A photosensitive member having a laminated photosensitive layer constituted of a charge generated layer and a charge transporting layer on an electrically conductive substrate, wherein the charge generating layer comprises a charge generating material selected from the group consisting of a bisazo pigment and a phthalocyanine and an additive selected from the group consisting of a phthaloperinone compound represented by the general formula [I] below, a phthaloperinone compound represented by the general formula [I']below, a naphthalimide compound represented by the general formula [II] and a naphthalimide compound represented by the general formula [II'] below:

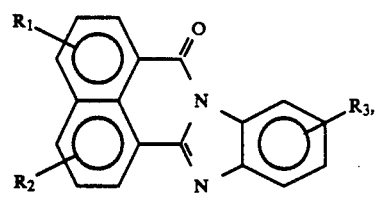

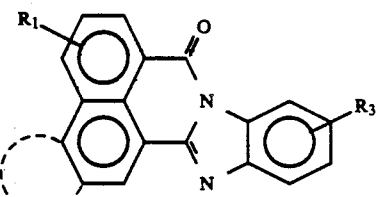

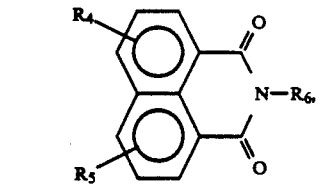

-continued
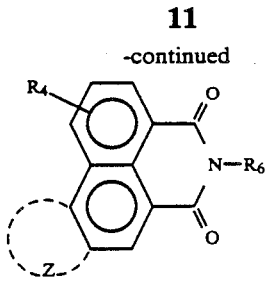
[II']
wherein $R_1$, $R_2$, $R_3$, $R_4$ and $R_5$ are respectively a hydrogen atom, an alkyl group, an amino group, a hydroxy group, a halogen atom, a nitro group, or a cyano group; $R_6$ is a hydrogen atom, an alkyl group or an aryl group; Z is a residual group forming a condensed aromatic cyclic ring with a benzene ring and Z may have a substituent.
* * * * *